United States Patent [19]

Coffey et al.

[11] 4,293,602

[45] Oct. 6, 1981

[54] NATURAL BOTANICAL ORNAMENT

[76] Inventors: James P. Coffey; Bettie L. Coffey, both of 137 South St., Ext., Warwick, N.Y. 10990

[21] Appl. No.: 104,010

[22] Filed: Dec. 17, 1979

[51] Int. Cl.³ .......................... A01N 3/00; A44C 25/00
[52] U.S. Cl. .................................. 428/28; 63/DIG. 2; 63/DIG. 3; 239/60; 264/DIG. 55; 428/421; 428/905
[58] Field of Search .................. 428/28, 905, 421, 422, 428/24; 63/DIG. 1, DIG. 2, DIG. 3; 264/DIG. 55; 239/60

[56] References Cited

U.S. PATENT DOCUMENTS

| 195,324 | 9/1877 | Atkinson | 63/23 X |
| 1,421,329 | 6/1922 | Welch | 63/2 |
| 3,553,296 | 1/1971 | Gaeckel | 525/240 X |
| 3,567,119 | 3/1971 | Wilbert | 428/18 X |
| 3,607,488 | 9/1971 | Yordan | 428/28 X |
| 3,660,115 | 5/1972 | Revis | 252/522 X |
| 3,828,577 | 8/1974 | Haynes | 63/2 |
| 3,997,686 | 12/1976 | McClure | 63/2 X |
| 4,020,156 | 4/1977 | Murray et al. | 252/522 X |
| 4,141,873 | 2/1979 | Dohany | 428/421 X |

FOREIGN PATENT DOCUMENTS

| 2052434 | 4/1972 | Fed. Rep. of Germany . |
| 2511212 | 9/1976 | Fed. Rep. of Germany . |
| 610105 | 5/1926 | France . |
| 650144 | 9/1928 | France .. |
| 684956 | 3/1930 | France . |

Primary Examiner—Henry F. Epstein
Attorney, Agent, or Firm—Bruce A. Yungman

[57] ABSTRACT

A fragrant ornament, such as a jewelry piece, is disclosed which consists of a mixture of a major amount of a natural botanical plant material, essential oils, and a minor amount of a fluorocarbon resin binder. A method for formulating and molding the ornament is also disclosed.

8 Claims, No Drawings

NATURAL BOTANICAL ORNAMENT

BACKGROUND OF THE INVENTION

1. Field of the Invention

This invention relates to an ornament or jewelery piece which emits a fragrance characteristic of a natural botanical material contained in the ornament. More particularly, this invention is directed to an ornament or jewelry piece which is formulated and molded from natural botanical materials and synthetic resins to provide the free release of fragrance from the botanical material. Such an ornamental molding exhibits the slow, long-term release of natural fragrance from the botanical constituent of the molding, as well as from particular essential oils incorporated in the molding.

The molded ornament can be utilized as a jewelry component, such as a bead or pendant, or as a display form or sculpture.

The invention also relates to a method for processing natural botanical materials, such as fragrant flowers and buds, into a dried, particulate constituent which is combined with complementary essential oils and a minor amount of a synthetic resin before molding into a fragment ornamental product. Such a fragrant ornamental product can be further shaped into beads, pellets and forms, which are suitable for jewelry, sculptures and display forms.

2. The Prior Art

Natural botanical materials have been used throughout history as fragrant ornamental devices, both on the person and as displays. However, these devices have always involved the natural form of the botanical materials, such as flowers for corsages, and table arrangements. The natural forms of these botanical materials have limited use because of their inability to be incorporated into jewelry and permanent displays, as well as their short useful life prior to wilting, decay and the termination of their natural fragrance.

Many attempts have been made to utilize flowers, leaves, bark, roots and herbs to provide a scented accent for personal wear or display. These attempts have produced products of uncertain structure and articles which lack the precise from for modern jewelry and the active wearing of present life styles. It would be useful and desirable to have natural botanical materials compounded with polymers to permit molding in precise forms. However, most polymers require high percentages of polymer to botanical material ratios and high heats of fusion, which together result in a plastic form with botanical materials as minor components.

In an attempt to avoid the deficiencies of the use of natural botanical materials to provide fragrances for ornaments and jewelry, the prior art has used the essential oils of such materials, as well as synthetically formulated perfumes, in inorganic fillers and inert ornamental structures to provide fragrant jewelry and ornaments.

In U.S. Pat. No. 3,553,296 to Jaeckel, an artificial flower is disclosed which is molded from a polyolefin powder that has previously been contacted with a perfume or essential oil. Such moldings have difficulty in producing the soft fragrance of natural materials and the qualities of plastic articles for display or ornamentation have limited public acceptance.

Natural biological materials have been suggested for use in jewelry in U.S. Pat. No. 3,997,686 to McClure. However, because animal excrement is the suggested jewelry component, natural fragrance is specifically discouraged. The patent teaches the coating of the excrement to protect against odor and an internal binder is not contemplated.

French Pat. No. 610,105 of Sept. 17, 1928 teaches the incorporation of a perfume, or the essence of a perfume, into an artificial pearl. This patent does not suggest the use of natural botanical materials as the substance of an artificial pearl.

Other prior art teachings of general interest are: U.S. Pat. No. 195,324 to Atkinson which discloses a porcelain structure which absorbs essential oils, U.S. Pat. No. 1,421,329 to Welch which describes jewelry having an encapsulated liquid, U.S. Pat. No. 3,828,577 to Haynes which shows a nasal ornament which can include a perfume ball of undisclosed structure, U.S. Pat. No. 4,020,156 to Murray et al which describes water soluble beads which release fragrance, German Pat. No. 2,052,434 of Apr. 27, 1972 which discloses a porous sintered metal which can absorb perfume, German Pat. No. 2,511,212 of Sept. 23, 1976 which shows jewelry with a special receptacle for the retention of perfume, and French Pat. No. 684,956 wherein an artificial pearl has perfme incorporated in the exterior coating or the entire structure thereof.

French Pat. No. 650,144 discloses a paste or liquid perfume encapsulated in jewelry.

These prior art teachings fail to disclose the use of natural botanical materials as a constituent of an ornament or jewelry piece wherein the materials impart their natural fragrance and texture to such devices. The prior art teachings require supplementary fragrance materials as the sole source of fragrance in the prior art devices. These shortcomings and others apparent in the prior art are overcome by the present invention which is described below.

SUMMARY OF THE INVENTION

The present invention consists of an ornament or jewelry component which exhibits the release of a natural fragrance over an extended period of time. The fragrance is derived from a natural botanical plant material, having an inherent fragrance, which is incorporated in a molding mixture for ornaments and jewelry pieces. The molding mixture also includes a minor amount of a fluorocarbon resin binder, which is sufficient to provide integral strength to the molded botanical material, and yet allows the free release of the fragrance from the materials. Essential oils which complement or bolster the naturally occurring fragrance are constituents in the ornaments and jewelry pieces. The essential oils can be incorporated with a fixative which absorbs the oils and acts as a carrier for the oils. The botanical materials also exhibit a natural fibrous texture in the finished ornament or jewelry piece.

The present invention also consists of a method of molding such ornamental pieces, wherein the natural botanical materials are comminuted into a particulate form in the presence of the essential oil prior to blending the particulate material with a fluorocarbon resin and molding and baking the same into a dry, finished fragrant product.

It is therefore an object of the present invention, as described above, to produce a naturally fragrant ornament with lasting qualities of shape retention, texture and long duration fragrance release.

It is an object of the present invention to select molding components for a natural botanical ornament, which components, in admixture, provide workability and moldability for making a variety of ornamental shapes and structures, while retaining the original natural fragrance of the botanical material.

It is a further object of the present invention to provide a fragrant ornament in which a natural botanical material is a major component and a resin binder is a minor component of said ornament.

These objects and others are achieved by the invention as set forth in greater detail as follows.

DESCRIPTION OF PREFERRED EMBODIMENTS

The naturally fragrant botanical ornaments of the present invention comprise compositions of various fragrant botanical materials in combination with essential oils, an optional fixative for such oils and a resin which binds these components together without preventing the release of the fragrance from the botanical materials and essential oils.

The natural botanical materials which are suitable for the fragrance imparting constituent of the present invention are selected from those plants having characteristic pleasant fragrances, such as, roses, lavender, citrus plants and tuberose. Specifically, only the aromatic parts of those plants are utilized. The flowers and buds of the plants are generally used. Accordingly, only the flowers or buds of citrus trees are prepared as the botanical materials for ornaments and jewelry.

Of particular interest to the selection of a fragrant source material are dried rose petals and buds of the seed bearing Dicotylendonous plants belonging to the order Rosales, genus Rosa. The Damask Rose of the Damascena Class is preferred, although other roses can be used in a similar manner depending on the fragrance perference.

Dried Lavender flowers and buds, specifically Lavandula vera and Lavenulas specia, can be used with equally satisfactory results. These flowers are from the Lavandula genus of the perennial aromatic plants in the Mint or Labiatae family. Other lavenders are also contemplated.

The dried flowers of the Tuberose (*Polianthes tuberosa*), a member of the amaryillis family (Amaryllidaceae) also gives good results as a natural botanical material source.

Finally, dried orange blossoms of the tropical and subtropical trees of the genus Citrus (Rutaceae family) can be used as naturally fragrant sources. The sweet or common orange blossom (*C. sinensis*) is preferred.

Other known naturally fragrant flowers, roots and herbs are also contemplated, and the present invention should not be deemed limited to the recited botanical materials. The botanical materials are used in amounts from 80 to 98 percent by weight.

All of these flowers are known for their natural fragrance retaining abilities, but in order to insure the retention of such fragrances, and in some cases, to complement such fragrances, it is the practice of the present invention to combine the essential oils of those plants from which flower or buds are taken, directly with those fragrant flowers or buds used as the botanical material, to reinforce the strength of the fragrance and extend the duration of the emission of the fragrance from the finished ornament or jewelry piece.

Essential oils are the concentrated extract of plants, which oils predominantly contain the complex chemicals responsible for the fragrances emitted by those plants. Essential oils are volatile, in that they release their components in vaporous form under standard conditions of temperature and pressure. Therefore, such oils are often referred to as volatile oils. The oils are derived from the various plant species by physical processes of separation and isolation. The oils generally consist of complex alcohols and aldehydes in various mixtures depending on the plant source. The oils are generally named for the species from which they are derived. Preferred essential oils for the present invention are Rose oil, Lavender oil, Tuberose oil and Orange Flower oil, all of which are used with their associated naturally fragrant botanical materials. The oils are used in amounts of 0.1 to 5 percent by weight.

The essential oils can be absorbed on the botanical material itself, or they can be absorbed on a fixative. A fixative is an absorbent which specifically retains the fragrance of the essential oil over an extended period of time. This function is achieved by equalizing the rate of evaporation of the fragrance agents. Preferred fixatives are: Vetiver (Kus-Kus) powder made from the dried root of Vetiveria Zizanioides stapf., Oak Moss, a lichen (*Evernia prunastri*) used in the form of a dried powder, and Orrisroot, a dried rhizome of the Iris, *I. germancia, I. florentina* and *I. pallioa*. Other natural fixatives can also be used with similar results. The fixative is used in an amount of from 0.0 to 5 percent by weight.

The resin binder, which is mixed with the natural botanical material and the essential oil, must bind the constituents together without masking or sealing in the fragrance of the constituents. Not all resins are capable of performing this objective. Fluorocarbon resins have been found to impart the necessary binding characteristics required in the present invention, while still providing for sufficient porosity in the finished product to allow for the emission of the fragrance compounds of the botanical materials and the essential oils and the exhibition of the texture of the botanical material.

The preferred fluorocarbon resin is Teflon 30 Suspension, a trademarked product, of DuPont Chemical Corp. This fluorocarbon resin is a suspension of 59% by weight of resin solids, 6.1% by weight wetting agents and 34.5% by weight of water. The resin is used in amounts of 1 to 10 percent by weight.

The use of a resin in suspension form is believed to assist in providing the dispersed nature of the resin in the finished product, with the result that the resin binds such constituents together, while allowing the porosity needed to release fragrance through the cured resin matrix. Optionally, a wetting agent can be incorporated in the mixture during the blending of the resin with the other constituents in order to assist the homogeneous blending of all components.

The molding mixture is formulated by first comminuting a naturally fragrant botanical material of flowers or buds, as specified above. The material is comminuted and mixed with an essential oil derived from the same botanical material or one that complements the fragrance of the natural botanical material. The essential oil can be absorbed on a fixative or it can be added directly to the botanical material and absorbed thereon. The comminution and mixing can be carried out in a shearing blender for 1 to 3 minutes until a medium fine powder (90% will pass through a 100 mesh screen) is achieved.

A fluorocarbon resin is then mixed with the comminuted mass in a shearing blender for 5 to 10 minutes. The objective of the resin blending is to create a fibrous dispersion, which will interlock and create a structure that binds the botanical material when molded. Lots of 200 to 500 grams are processed in this manner. These lots are combined in a jar equipped with tumbling wires. The filled jars are rotated for 1 to 4 hours to maintain the consistency of the molding mixture as it is produced in batch form. Larger lots or a continuous processing can be achieved with appropriate equipment with similar results.

The resulting molding mixture is a damp dough that is subsequently molded in compression molds or by extraction through a die. The mold pressures can be from 4000 to 10,000 psi. The molded mixture is then baked by heating to the curing temperature of the resin, which should be well below the temperature of degradation of the botanical materials and the essential oils. The curing temperature is preferably in the range of 150° to 200° F. The baking step is performed for approximately 30 minutes or until the resin is fully cured.

The molded ornament is then drilled, bonded, or glued to suitable jewelry findings or displays. Extruded stock can be cut to length and used as beads or jewelry components.

The present invention will be more fully described by reference to the following working example, which illustrates a preferred embodiment.

EXAMPLE

A dried rose ornament was prepared by weighing 95 grams of a mixture of rose petals and buds. The mixture was placed in a shearing blender. A 1 gram tincture of Rose oil was absorbed on 1 gram of Kus-Kus powder and added to the blender. The blender was operated for approximately 3 minutes, at which time the mixture was reduced to a powder. The powder passed through a 100 mesh screen.

To this initial mixture, 8.6 grams of Teflon 30 Suspension was added. The blender was reoperated for approximately 10 minutes to thoroughly mix and fibrillate the resin through the rose mixture.

The composite mixture was then weighed and filled into a jewelry mold of cylindrical shape. The mixture was molded under a pressure of 6000 psi. The mold and the compressed mixture were then heated to 150° F. and this temperature was maintained for 30 minutes. The mold was cooled and opened to remove a textured, fragrant rose ornament of solid structure.

In general, the compositions of the present invention can be formulated in a range as follows:

80% to 98% dried botanical materials
0.1% to 5.0% essential oils
0.0% to 5.0% fixative
1.0% to 10% fluorocarbon resin.

The preferred range for the compositional formulation is
95% dried botanical materials
0.1% essential oil
1.0% fixative
3.36% fluorocarbon resin
0.34% wetting agent.

Natural botanical ornaments and jewelry made according to the above-described method and formulations have retained their fragrance for over a year when stored in an air-tight container and periodically exposed to ambient conditions for 24 hours every 5 to 7 days.

The rose ornaments have been found to last up to six months under continuous ambient conditions before the fragrance weakens. The lavender ornaments have retained their full strength fragrance for up to nine months under similar conditions.

While particular embodiments of the present invention have been described in detail, it is apparent that adaptations and modifications may occur to those skilled in the art. Such adaptations and modifications may be made without departing from the true spirit and scope of the present invention, as set forth in the claims.

What is claimed is:

1. A fragrant ornament molded in a compression molding process from a mixture comprising, in combination:
   (a) a naturally fragrant botanical material comminuted into a particulate form,
   (b) an essential oil, which is capable of complementing the fragrance of said botanical material, and which is absorbed on the botanical material or an optional absorbtive fixative, and
   (c) a fiber reinforced fluorocarbon resin binder, which binds the botanical material together without masking or sealing the botanical material, allowing the release of the fragrance from said botanical material and said absorbed essential oil, said resin binder being dispersed through the botanical material from an aqueous suspension of the fluorocarbon resin.

2. The invention of claim 1 wherein the ornament consists of a jewelry piece.

3. The invention of claim 1 wherein the botanical material is chosen from the group consisting of rose petals and buds, lavender flowers and buds, tuberose flowers and orange blossoms.

4. The invention of claim 1 wherein the essential oil is chosen from the group consisting of Rose oil, Lavender oil, Tuberose oil and Orange Flower oil.

5. The invention of claim 1 wherein the fixative is a dried powder selected from the group consisting of the root of the plant Vetiveria Zizanicoides stapf., and oak moss lichen Evernia Prunastri, and Orrisroot.

6. A fragrant ornamental jewelry piece molded in a compression molding process from a mixture comprising in combination:
   (a) 80% to 98% by total weight, of a dried, naturally fragrant, botanical material comminuted into a particulate form,
   (b) 0.1% to 5.0% by total weight of an essential oil which is capable of complementing and bolstering the fragrance of said botanical material,
   (c) 1.0% to 10% by total weight of a fiber reinforced fluorocarbon resin, which functions as a binder for said botanical material without masking or sealing the botanical material and allows for the natural release of the fragrance from said botanical material and said essential oil, said resin binder being dispersed through the botanical material from an aqueous suspension of the fluorocarbon resin, and
   (d) 1.0% to 5.0% of a natural fixative, in powder form, for absorbing said essential oil in said mixture.

7. The invention of claim 6 wherein the jewelry piece contains from 95% to 98% by total weight of said botanical material.

8. The invention of claim 7 wherein the jewelry piece contains from 2% to 5% by total weight of said fluorocarbon resin.

* * * * *